United States Patent
Viswanathan et al.

(10) Patent No.: US 9,345,996 B2
(45) Date of Patent: May 24, 2016

(54) LIQUEFIED PETROLEUM GAS FILTRATION SYSTEM

(75) Inventors: Karthik Viswanathan, Minneapolis, MN (US); Philip Edward Johnson, Apple Valley, MN (US); Dustin Zastera, Hastings, MN (US); James Doyle, St. Louis Park, MN (US); Gregory L. LaVallee, Monticello, MN (US); Janelle M. Hampton, Burnsville, MN (US)

(73) Assignee: Donaldson Company, Inc., Minneapolis, MN (US)

( * ) Notice: Subject to any disclaimer, the term of this patent is extended or adjusted under 35 U.S.C. 154(b) by 546 days.

(21) Appl. No.: 13/481,429

(22) Filed: May 25, 2012

(65) Prior Publication Data

US 2013/0134110 A1    May 30, 2013

Related U.S. Application Data

(60) Provisional application No. 61/489,938, filed on May 25, 2011.

(51) Int. Cl.
*B01D 29/56* (2006.01)
*C07C 7/12* (2006.01)
*C07C 7/13* (2006.01)
*B01D 29/60* (2006.01)
*B01D 35/143* (2006.01)

(52) U.S. Cl.
CPC .............. *B01D 29/56* (2013.01); *B01D 29/606* (2013.01); *B01D 35/143* (2013.01); *C07C 7/12* (2013.01); *C07C 7/13* (2013.01)

(58) Field of Classification Search
CPC .... B01D 29/56; B01D 35/143; B01D 29/606; C07C 7/12; C07C 7/13; C10G 25/003
USPC ...................................................... 210/90, 690
See application file for complete search history.

(56) References Cited

U.S. PATENT DOCUMENTS

| | | | |
|---|---|---|---|
| 4,332,679 A | 6/1982 | Hengst et al. | |
| 4,534,865 A * | 8/1985 | Sundberg et al. | ............. 210/692 |
| 4,685,066 A | 8/1987 | Hafele et al. | |
| 4,743,374 A | 5/1988 | Stifelman | |
| 5,474,671 A * | 12/1995 | O'Connor ............ | C10G 25/003 208/299 |

(Continued)

FOREIGN PATENT DOCUMENTS

| | | |
|---|---|---|
| EP | 0408758 | 1/1991 |
| WO | 2012/162662 | 11/2012 |

OTHER PUBLICATIONS

Ramakrishna et al., "An Introduction to Electrospinning and Nanofibers," National University of Singapore, World Scientific, Chapter 5, date unknown, 14 pages.

(Continued)

*Primary Examiner* — Matthew O Savage
(74) *Attorney, Agent, or Firm* — Pauly, DeVries Smith & Deffner, LLC

(57) ABSTRACT

Described herein are filter assemblies for removing high molecular weight organic components from liquefied petroleum gas, as well as methods for removing high molecular weight components from liquefied petroleum gases. The filter assemblies include an upstream carbon-containing filter media pack and a downstream filter media pack.

12 Claims, 9 Drawing Sheets

(56) References Cited

U.S. PATENT DOCUMENTS

| | | |
|---|---|---|
| 6,645,271 B2 | 11/2003 | Seguin et al. |
| 6,743,273 B2 | 6/2004 | Chung et al. |
| 7,309,372 B2 | 12/2007 | Kahlbaugh et al. |
| 7,314,497 B2 | 1/2008 | Kahlbaugh et al. |
| 7,641,055 B2 | 1/2010 | Ferrer et al. |
| 7,655,070 B1 | 2/2010 | Dallas et al. |
| 2003/0192830 A1* | 10/2003 | Memmott et al. ............ 210/663 |
| 2011/0198280 A1 | 8/2011 | Jones et al. |

OTHER PUBLICATIONS

International Search Report and Written Opinion for PCT/US2012/039703 mailed Feb. 25, 2013, 16 pages.

International Preliminary Report on Patentability for PCT/US2013/039703, mailed Dec. 5, 2013 (11 pages).

* cited by examiner

LIQUEFIED PETROLEUM GAS FILTRATION SYSTEM

This application claims the benefit of U.S. Provisional Application No. 61/489,938, filed May 25, 2011, the contents of which are herein incorporated by reference.

FIELD OF THE INVENTION

The invention described herein relates to a filtration system. In particular, the invention relates to a filtration system for the removal of high molecular weight organic compounds from liquefied petroleum gas.

BACKGROUND OF THE INVENTION

Crude oil contains many different hydrocarbon compounds. The major compounds include petroleum gas, which includes small alkanes and alkenes ($C_1$-$C_4$), such as methane, ethane, propane, propylene, butane, and butylene; naphtha, which includes intermediate hydrocarbons ($C_5$-$C_9$); kerosene, a liquid mixture of $C_{10}$-$C_{18}$ alkanes and aromatics; diesel oil, which includes liquid alkanes containing twelve or more carbon atoms; lubricating oil, which includes long chain ($C_{20}$-$C_{50}$) alkanes, cycloalkanes, and aromatics; and fuel oil, which includes long chain ($C_{20}$-$C_{70}$) alkanes, cycloalkanes, and aromatics, along with various solid residuals such as coke, asphalt, tar, and waxes. The various hydrocarbon compounds are typically separated by fractional distillation.

Liquefied petroleum gas (also called LPG) refers to a flammable mixture of $C_1$-$C_4$ hydrocarbons that exists as a liquid at or below about −42° C., or when stored under pressure. At atmospheric pressure and temperatures above about −42° C., LPG is a colorless and odorless gas. As with natural gas, an identifying odorant, such as ethyl mercaptan, is typically added so that leaks of LPG can be more easily detected. Since LPG is substantially more compact as a liquid than as a gas, it is typically stored and transported under pressure (about 1725 kilopascals) where it exists as both a liquid and vapor.

Some LPG fuel systems include a filter to remove small particulate material from the fuel. However, a brown greasy or waxy material can still build up in the fuel system, for example, in the vaporizer (sometimes called a converter), downstream in the vapor hose, in the carburetor, and in the valves or mixer. The build-up is due to trace amounts of high molecular weight materials (also called greases, waxes or heavies) in the LPG acquired during refining, distribution and/or storage. When the LPG is vaporized, these high molecular weight materials can precipitate out of the vapor stream, often resulting in deposits that can obstruct injectors, valves, vaporizers or other components and can interfere with the operation of the fuel system. This can result in additional maintenance, shutdowns, and increased costs.

Therefore, a need exists for a system that can reduce the deposit of high molecular weight materials on LPG fuel system components while still removing particulate contaminants.

SUMMARY OF THE INVENTION

Described herein are filter assemblies for removing high molecular weight organic components from liquefied petroleum gas, as well as methods for removing high molecular weight components from liquefied petroleum gases. The filter assemblies can include, in some implementations, two separate filter media packs: A first filter media pack is configured to remove high molecular weight compounds from liquefied petroleum gases. This first filter media pack is typically configured so that even after it reaches capacity for holding high molecular weight compounds, liquefied petroleum gases can still readily pass through the filter media. This first filter media pack is configured to readily load significant quantities of high molecular weight contaminants without excessive restriction of flow upon reaching capacity. The second filter media pack, which is positioned downstream from the first media pack, is also configured to load high molecular weight contaminants, although typically significantly lower quantities than the first media pack. However, unlike the first media pack, the second media pack is generally configured to have a very significant increase in restriction of flow upon loading with high molecular weight hydrocarbons. Thus, unlike the first media pack, in certain embodiments the downstream media pack significantly restricts flow of the liquefied petroleum gas once the downstream media pack has loaded with high molecular weight contaminants. In particular, once the downstream media pack has loaded to near theoretical capacity with high molecular weight contaminants it provides a significant resistance to fluid flow. As used herein, theoretical capacity refers to the total change in mass of the filter media pack upon prolonged exposure to LPG containing high molecular weight hydrocarbons. Generally such capacity is measured at the saturation point of the media, which is where the quantity of adsorbed and retained high molecular weight hydrocarbons is no longer increasing. In practice the media may continue to very gradually pick up small quantities of high molecular weight hydrocarbons once it approaches saturation, and therefore another capacity measure is "functional capacity". Functional capacity is the point where saturation of the media is substantially reached, where the pickup of contaminants typically has slowed down dramatically, and where high molecular weight contaminants readily pass through the filter media. Thus, functional capacity is reached at the point were significant contaminant breakthrough occurs. Functional capacity is generally not materially different than the theoretical capacity. In fact, the two are often very similar. However, the term "functional capacity" can be used to clarify that full theoretical capacity is in some regards a hypothetical concept because media can continue to load even trivial, all-but-unmeasurable amounts of contaminants for a long period of time after any functional benefit of filtration has diminished completely.

Typically the first filter media pack (the upstream media pack) has a much higher capacity to retain high molecular weight contaminants than the downstream filter media pack. The upstream media pack can include activated carbon, such as a packed carbon bed, that has relatively high capacity for adsorbing and retaining high molecular weight contaminants. The second filter media pack (the downstream media pack) can be formed of a material comprising a fine fiber, such as nanofiber. The downstream media pack generally has a relatively low capacity for adsorbing and retaining high molecular weight contaminants relative to the upstream media pack, but upon reaching capacity it provides a restriction to flow of liquid through the media pack.

Thus, the upstream media pack performs a primary function of reducing contaminants in the liquefied petroleum gas. The downstream media pack's primary function is to rapidly provide resistance to fluid flow once it is exposed to high molecular weight contaminants due to the performance of the upstream media pack diminishing. Thus, once the upstream media pack approaches or reaches capacity, and high molecular weight contaminants flow through this upstream media pack, the downstream media pack quickly reaches a point of sufficient loading that fluid flow through the filter assembly is meaningfully impeded. This impedance to flow can be measured by a change in pressure differential from the upstream to downstream side of the media packs. In this manner, the downstream (or second) filter media pack serves as an end of life indicator for the filter assembly by restricting flow once the upstream (or first) filter media pack is no longer adequately removing the high molecular weight contaminants.

In an example embodiment the first filter media pack is configured to exhibit a change in upstream to downstream pressure differential of less than 200 percent upon reaching saturation for retaining high molecular weight compounds, and the second filter media pack is configured to exhibit a change in upstream to downstream pressure differential of greater than 200 percent upon reaching saturation of high molecular weight compounds. The second filter media pack may be configured to exhibit a change in upstream to downstream pressure differential of greater than 400 percent upon reaching saturation of high molecular weight compounds. The first filter media pack can be arranged in an open channel configuration to further avoid flow restrictions upon reaching capacity.

In addition, further elements can be added to the assembly. For example, a third media pack can be added to remove particulate contaminants (and also to optionally remove carbon or other material which has the potential to bleed from the first filter media pack). The third filter media pack can have a mean flow pore size of 10 microns or less, for example. In some implementations the third filter media pack has an efficiency of at least 99.9 percent for removal of particulate contaminants having an average particle size of 5 microns. The particulate filter can be positioned, for example, upstream of the first and second filter media packs, between the first and second filter media packs, or downstream from both the first and second filter media packs.

In an example embodiment the filter assemblies include an upstream carbon-containing filter element and a downstream end-of-life indicator comprising a fine fiber web. In one embodiment, the carbon-containing filter element includes activated carbon derived from wood, coconut or coal that has a surface area of at least about 500 m$^2$/g and an average pore size of at least about 20 Angstroms (measured using BET surface analysis, described below, which measures pore volume). The activated carbon can be, for example, powdered or granular, or a combination thereof.

In some implementations the second filter media pack has a total capacity for retaining high molecular weight hydrocarbons that is no more than 5 percent of the total capacity of the first filter media pack for retaining high molecular weight hydrocarbons. The second filter media pack can comprise a fine fiber web. Suitable fine fiber webs include those with a pore size of no more than about 25 microns (measured using scanning electron microscopy analysis, described below). Second filter media packs with a pore size of no more than about 10 microns are suitable for some embodiments.

A filter assembly for filtering high molecular weight compounds from liquefied petroleum gas is also disclosed in which the filter assembly includes a first filter media pack configured to remove high molecular weight compounds, the first filter media pack having a first total capacity for retaining high molecular weight hydrocarbons; and a second filter media pack configured to remove high molecular weight compounds, the second filter media pack located downstream from the first filter media pack, the second filter media pack having a second total capacity for retaining high molecular weight hydrocarbons. The second filter media pack has a total capacity for retaining high molecular weight hydrocarbons that is no more than 10 percent of the total capacity of the first filter media pack for retaining high molecular weight hydrocarbons, and the second filter media pack demonstrates at least a 25 percent increase in resistance to flow of liquefied petroleum gas upon or before reaching total capacity. In some implementations that increase in resistance to flow is at least 50 percent, alternatively at least 100 percent, optionally at least 200 percent, and in other implementations at least 400 percent.

Optionally a third filter media pack is positioned intermediate the first filter media pack and the second filter media pack, the third filter media pack having an efficiency of at least 99.9 percent for removal of particulate contaminants having an average particle size of 5 microns. The third filter media pack intermediate the first filter media pack and the second filter media pack can have a mean flow pore size of less than 10 microns in some embodiments (measured using, for example, an automated air permeability porometer manufactured by Porous Materials, Inc.).

The first filter media pack can include activated carbon, such as activated carbon having a surface area of at least about 500 m$^2$/g and an average pore size of at least about 20 Angstroms. In some implementations the second filter media pack has a total capacity for retaining high molecular weight hydrocarbons that is no more than 2 percent of the total capacity of the first filter media pack for retaining high molecular weight hydrocarbons, and can have an open channel configuration. Suitable media for the first filter media pack also includes carbon fibers. The second filter media pack may include a fine fiber web, such as a fine fiber web with a pore size of no more than about 25 microns. Alternatively, the second filter media pack comprises a fine fiber web with a pore size of no more than about 10 microns.

Further, a filter assembly for filtering high molecular weight compounds from liquefied petroleum gas is disclosed in which a first filter media pack is configured to remove high molecular weight compounds such that initial efficiency for removal of high molecular weight hydrocarbons from a liquefied petroleum gas is at least 80 percent at high molecular weight hydrocarbon concentrations of up to 0.5 percent by weight. The first filter media pack has a first total capacity for retaining high molecular weight hydrocarbons. A second filter media pack is configured to also remove high molecular weight compounds. The second filter media pack is located downstream from the first filter media pack. The second filter media pack has an initial efficiency at removing of high molecular weight hydrocarbons of at least 80 percent at original concentrations of up to 0.5 percent by weight of the liquefied petroleum gas, the second filter media pack having a second total capacity for retaining high molecular weight hydrocarbons that is no more than 10 percent of the first total capacity of the first filter media pack. In certain embodiments the second filter media pack demonstrates an increased resistance to flow of liquefied petroleum gas of at least 25 percent upon or before reaching total capacity.

Methods for determining service life of a filter assembly configured to remove high molecular weight hydrocarbons from liquefied petroleum gas are also disclosed. The methods can use any of the filter assemblies and media packs described herein. In an example implementation, the method includes providing a first filter media pack and passing liquefied petroleum gas through it such that at least 80 percent of initial high molecular weight hydrocarbons are removed. A second filter media pack is located downstream from the first filter media pack. When passing the liquefied petroleum gas through the second filter media pack, the second filter media pack retains at least 50 percent of remaining high molecular weight hydrocarbons that have passed through the first media pack. The second filter media pack has a total capacity for retaining high molecular weight hydrocarbons that is no more than 10 percent of the total capacity of the first filter media pack, wherein the second filter media pack demonstrates an increased resistance to flow of liquefied petroleum gas of at least 50 percent upon or before reaching total capacity.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention will now be described in regards to the Figures, in which.

Figure 1:
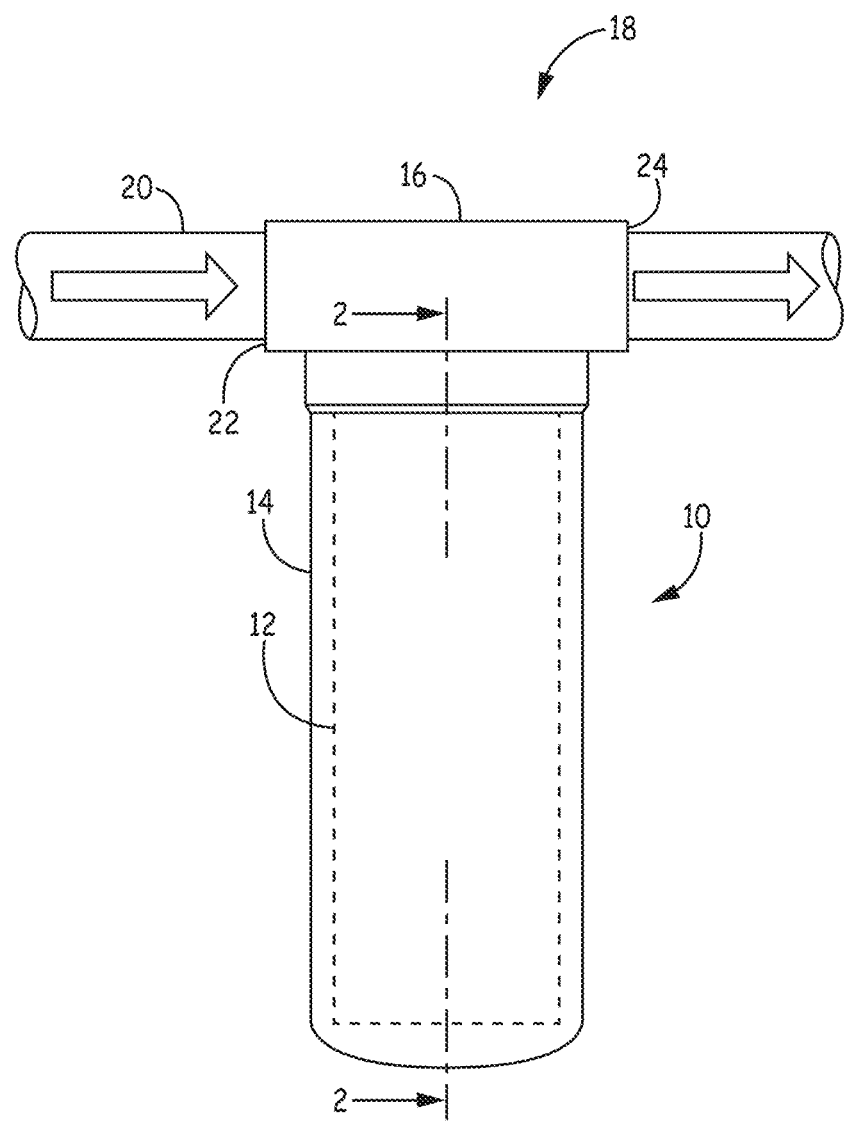
FIG. 1 is a schematic of one embodiment of a filter assembly constructed and arranged in accordance with an implementation of the invention.

While the invention is susceptible to various modifications and alternative forms, specifics thereof have been shown by way of example and drawings, and will be described in detail. It should be understood, however, that the invention is not limited to the particular embodiments described. On the contrary, the intention is to second modifications, equivalents, and alternatives falling within the spirit and scope of the invention.

DETAILED DESCRIPTION

Described herein is a system for removal of contaminants from liquefied petroleum gas (LPG), in particular a filtration system that adsorbs, separates, and/or filters out high molecular weight organic materials from LPG. These high molecular weight organic materials can build-up in a fuel system unless removed.

More particularly, the system described herein removes high molecular weight organics that are acquired through refining, distribution, and storage. The system reduces build-up of deposits in the LPG fuel system injectors, valves, vaporizers or other components. The systems and methods described herein are suitable for use with a variety of grades of LPG, including, for example, commercial grade propane; engine fuel-grade propane (also known as HD-5 propane); and commercial grade butane.

The systems and methods can be used at a variety of locations in the LPG fuel supply chain, under a variety of conditions, including, but not limited to: oil refinery or natural gas processing plants; during shipping, including on highway transport trucks (which typically carry from about 25,000 to 50,000 liters of LPG) and on smaller bulk delivery trucks (which typically carry from about 4,000 to 20,000 liters of LPG and dispense LPG at a flow rate from about 75 liters per minute (LPM)), up to about 200 LPM; during storage in "bulk plants" (retail propane storage facilities); at a dispenser storage tank, for example, a propane tank and/or pump at a service station that is used to fill propane cylinders (which typically dispense LPG at a flow rate of as little as about 20 LPM, and up to about 50 GPM); or at the point of use, for example, in the fuel supply on an engine (which can move LPG at a flow rate of as little as 4 liters per hour (LPH), or up to about 40 LPH, or up to 60 LPH.

The contaminants removed by the systems and methods include, but are not limited to, high molecular weight organic materials, such as hydrocarbons with more than 16 carbon atoms (greater than $C_{16}$), or between about $C_{20}$ to about $C_{60}$ or more than about $C_{60}$. In particular, contaminants which are removed include high molecular weight organic materials that are at least partially soluble in LPG.

The systems and methods are capable of adsorbing, separating and/or filtering out high molecular weight components from LPG, without removing excessive amounts odorant, such as ethyl mercaptan, which is frequently included in LPG as a safety precaution. In general, ethyl mercaptan is added in an amount of at least about 35 ppm and is considered non-detectable at levels below 12 ppm. In one embodiment, substantially no mercaptan is removed by the filter system. In other implementations less than 50 percent of mercaptan is removed, optionally less than 25 percent of mercaptan is removed, and desirably less than 10 percent of mercaptan is removed.

In one embodiment, the filter system is configured as a single pass filter, for example, a filter used during bulk fill or bulk dispensing. In a more particular embodiment, the filter system can be configured as a cartridge (or replaceable element) filter, in which a permanent housing contains a replaceable filter element or cartridge. In an alternate embodiment, the filter system is configured as a spin-on filter, in which a self-contained housing and element assembly is unscrewed from its mount, discarded and replaced with a new housing and filter assembly.

The filter systems can include, in some implementations, two separate filter media packs: A first filter media pack is configured to remove high molecular weight compounds from liquefied petroleum gases. This first filter media is typically configured so that even once it reaches capacity for holding high molecular weight compounds, liquefied petroleum gases can still readily pass through the filter media. Thus, this first filter media is configured to readily load significant quantities of high molecular weight contaminants without excessive restriction of flow upon reaching capacity. The second filter media pack is positioned downstream from the first media pack. Unlike the first media pack, in certain embodiments the downstream media pack significantly restricts flow of the liquefied petroleum gas once the downstream media pack has loaded with high molecular weight contaminants. In particular, once the downstream media pack has loaded to near capacity with high molecular weight contaminants it provides a significant resistance to fluid flow.

Typically the first filter media pack (the upstream media pack) has a much higher capacity to retain high molecular weight contaminants than the downstream filter media pack. The upstream media pack can include activated carbon, such as a packed carbon bed, that has relatively high capacity for adsorbing and retaining high molecular weight contaminants. The second filter media pack (the downstream media pack) can be formed of a material comprising a fine fiber, such as nanofiber. The downstream media pack has a relatively low capacity for adsorbing and retaining high molecular weight contaminants, but upon reaching capacity it provides a restriction to flow of liquid through the media pack.

Thus, in use the upstream media pack performs a primary function of reducing contaminants in the liquefied petroleum gas. The downstream media pack's primary function is to rapidly provide resistance to fluid flow as quickly as possible after it is exposed to high molecular weight contaminants. Thus, once the upstream media pack approaches or reaches capacity, and high molecular weight contaminants flow through this upstream media pack without being retained, the downstream media pack quickly reaches a point of sufficient loading that fluid flow through the filter assembly is meaningfully impeded (and potentially completely stopped). In this manner, the downstream (or second) filter media pack serves as an end of life indicator for the filter assembly by restricting flow once the upstream (or first) filter media pack is no adequately removing the high molecular weight contaminants.

In addition, further elements can be added to the assembly. For example, a particulate filter in a third media pack can be added to remove particulate contaminants (and also to optionally remove carbon or other adsorbent that is released from the first filter media pack). The third filter media pack can have a mean flow pore size of 10 microns or less, for example. Such pore testing can be accomplished utilizing, for example, an automated air permeability porometer manufactured by Porous Materials, Inc., as described in U.S. Patent Publication No. 2011/0198280, incorporated herein by reference in its entirety. The particulate filter can be positioned, for example, upstream of the first and second filter media packs, between the first and second filter media packs, or downstream from both the first and second filter media packs.

Filter Assembly Configuration

Now, in reference to the drawings, one embodiment of a filter system 18 is shown in FIG. 1. Although other configurations are possible, in the embodiment shown in FIG. 1 the filter system includes a filter assembly 10 that includes a generally cylindrical housing 14 that defines a chamber in which a filter element 12 is positioned. In this embodiment, housing 14 is constructed from a thin-walled material, such as metal or other synthetic material, that is capable of withstanding pressures of at least about 500 kilopascals, or between about 1000 kilopascals and 2000 kilopascals, and up to 3000 kilopascals. In one embodiment, the housing 14 can be formed from deep drawn steel with a wall thickness between about 0.25 millimeters and 2.5 millimeters, or between about 0.5 millimeters and 1.25 millimeters.

In the depicted embodiment, the filter assembly 10 is operably mounted to a filter block or filter head 16, typically by screwing the filter assembly 10 onto the filter head 16 by internal threads on the filter assembly 10. The filter system 18 includes a supply 20 for supplying fluid to the filter assembly 10 through an inlet 22 of the filter head 16. The fluid enters and is filtered by the filter element 12 and exits the filter head 16 at an outlet 24 of the filter head 16 and is carried away by a passage 26. It will be understood that filter assembly 10 is depicted in an example configuration, and that numerous other configurations are possible for filter assemblies without deviating from the scope of the invention.

Figure 2:
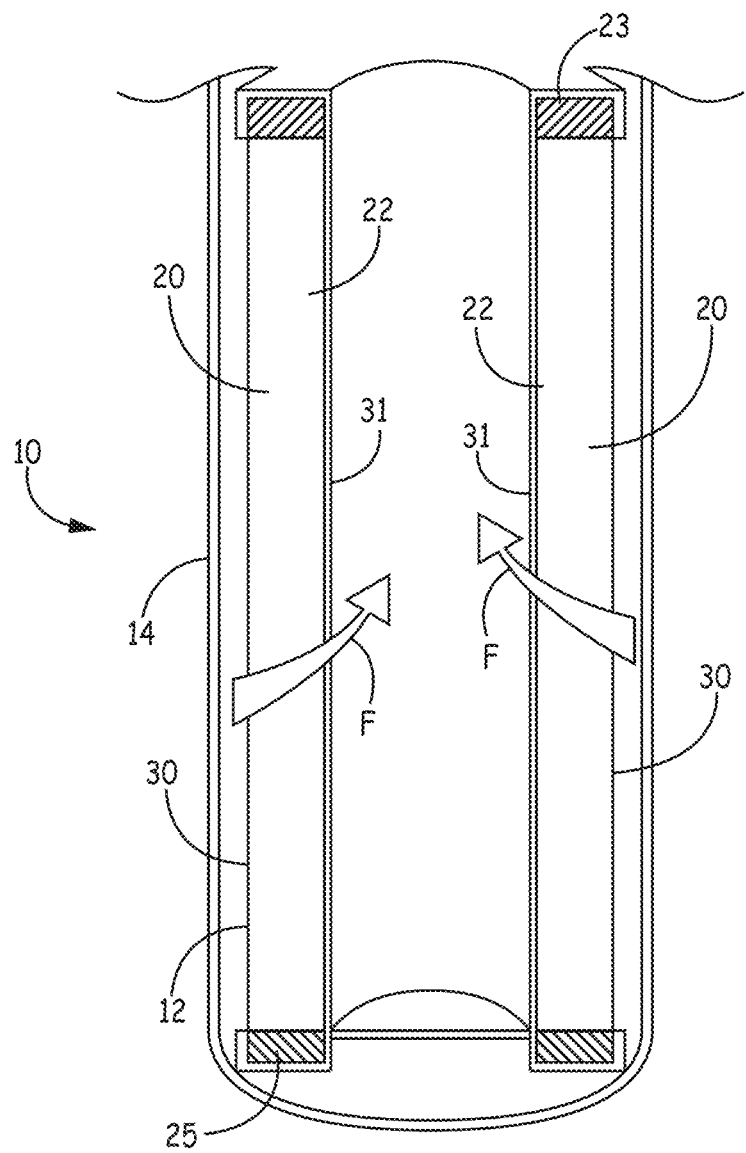
FIG. 2 is a cross-sectional view of the filter assembly of FIG. 1 taken along line 2-2.

FIG. 2 shows a cross-sectional view of the filter assembly 10 of FIG. 1 taken along line 2-2, in which the filter element 12 includes a generally cylindrical filter medium, supported within the canister via one or more end caps 23, 25 such that unfiltered fluid flows through the filter medium in a generally radial direction. In the embodiment shown in FIG. 2, the LPG fuel follows an outside/in pattern in which LPG fuel passes from an outer surface 30 of the filter 12 towards an inner surface 31 of the filter 12, as shown by the arrows marked "F" in FIG. 2. However, it also possible to design the filter assembly 18 such that the fuel follows an inside/out pattern in which the fuel passes from an inner surface of the filter towards an outer surface of the filter (not shown). In the embodiment shown in FIG. 2, the outer surface 30 is "upstream" and the inner surface 31 is "downstream" with respect to the direction of the fuel flow.

Figure 3:
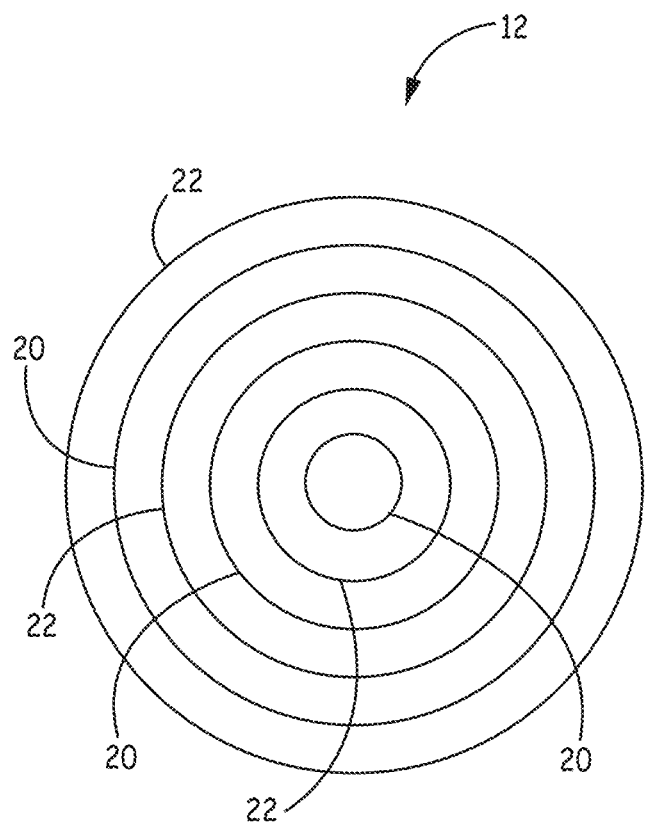
FIG. 3 is a cross-sectional view of an alternative filter assembly constructed and arranged in accordance with an implementation of the invention.

In an alternative embodiment, shown in FIG. 3, the filter element 18 includes multiple layers of carbon-containing filter element 20 and end-of-life indicator layers 22, e.g., anywhere from 2 to 50 layers, wherein each "layer" includes a carbon-containing filter element and an end-of-life indicator layer.

Figure 4A:
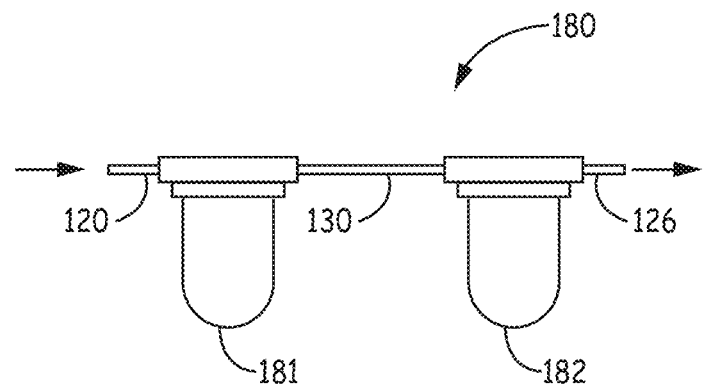
FIG. 4A is a schematic of an embodiment of a filter assembly constructed and arranged in accordance with an implementation of the invention.

FIG. 4A shows a filter system 180 which includes a primary filter 181 and secondary filter 182. The LPG fluid enters the primary filter 181 of the system through supply 120. After passing through the primary filter 181, the LPG is transported to the secondary filter 182 by conduit 130. Once the LPG crosses the secondary filter 182, it exits the system via passage 126. In the dual-filter embodiment shown in FIG. 4A, the primary filter 181 includes a housing in which a carbon-containing filter element is located.

The secondary filter 182 includes a housing in which a fine fiber web is located, wherein the fine fiber web is configured to entrap "breakthrough" high molecular weight organics that are not adsorbed by the primary filter. As described above, the "breakthrough" high molecular weight organics form a film on the fiber web, which increases backpressure and serves as a fuse to determine end-of-life. If desired, the system can also include one or more downstream particulate filters configured to remove particulates, such as carbon particulates, from the LPG stream.

Figure 4B:
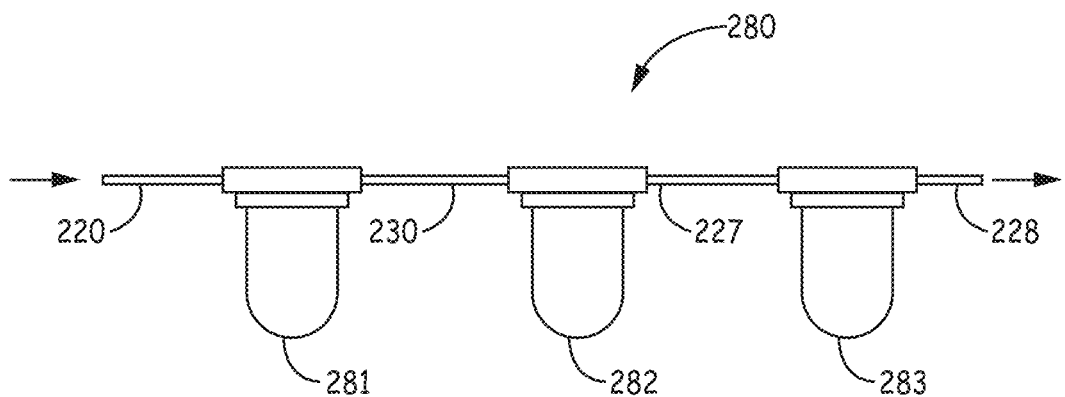
FIG. 4B is a schematic of an embodiment of a filter assembly constructed and arranged in accordance with an implementation of the invention.

FIG. 4B shows a filter system 280 which includes a first filter 281, a second filter 282, and a third filter 283. The LPG fluid enters the first filter 281 of the system through supply 220. After passing through the first filter 281, the LPG is transported to the second filter 182 by conduit 230. Once the LPG crosses the second filter 282, it passes to third filter 284 via conduit 227 before exiting the system via passage 228. In the filter embodiment shown in FIG. 4B, the filter 281 includes a housing in which a carbon-containing filter element is located, the second filter 282 includes a housing in which a particulate fiber is located, and the third filter 283 includes a housing in which a fine fiber web is configured to entrap "breakthrough" high molecular weight organics that are not adsorbed by the primary filter. As described above, the "breakthrough" high molecular weight organics form a film on the fiber web, which increases backpressure and serves as a fuse to determine end-of-life.

Figure 5A:
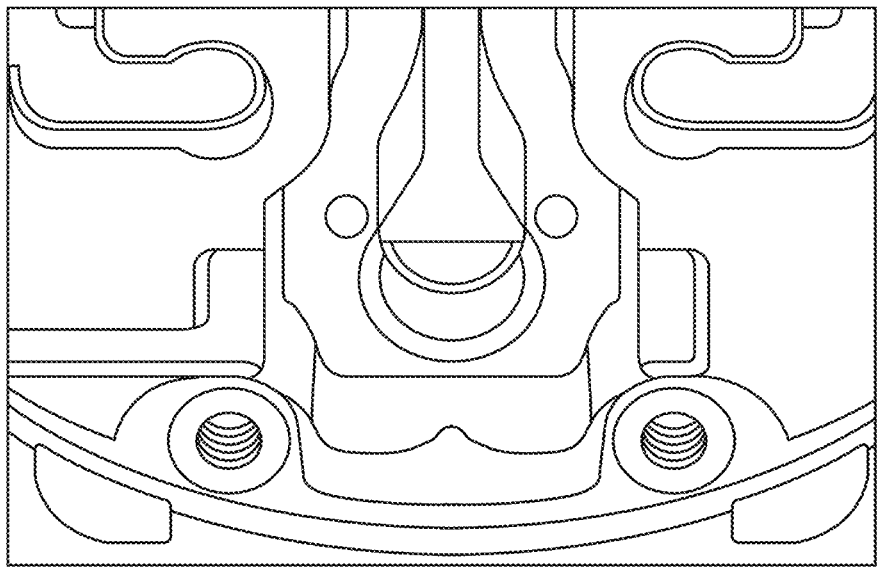
FIG. 5A is a photograph of the interior of regulator assembly in a LPG distribution device which has been used with unfiltered LPG liquids, the regulator assembly showing a deposit of high molecular weight hydrocarbons.
Figure 5B:
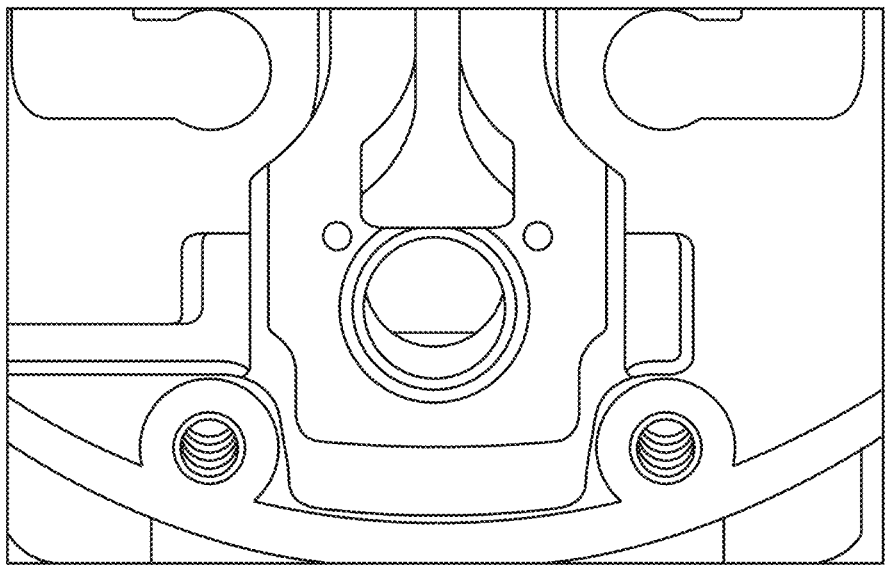
FIG. 5B is a photograph of the interior of regulator assembly in a LPG distribution device, which has been used with LPG liquids filtered in accordance with the teachings herein, the regulator assembly showing no visible deposit of high molecular weight hydrocarbons.

FIG. 5A and FIG. 5B shows photographs of the interior of an LPG handling assembly after prolonged exposure to liquefied petroleum gases. In FIG. 5A, the liquefied petroleum gas has not been filtered using an assembly as described herein. In FIG. 5B the liquefied petroleum gas has been filtered using an assembly as described herein. Deposits of contaminant materials, identified as high molecular weight hydrocarbons, have formed in assembly. Such deposits eventually become so significant so as to diminish performance of the regulator, and can ultimately fully obscure fuel flow paths.

Upstream Adsorbent Material

A variety of adsorbent materials are suitable for the upstream adsorbent media pack. In particular, carbon-containing filter elements are suitable for use in the system of the invention. In general, a carbon-containing filter element containing carbon media with a high surface area and an open pore structure, such as activated carbon, is effective for adsorbing high molecular weight organic impurities from LPG.

In general, LPG that includes more than about 0.25% volume/volume high molecular weight organic impurities is unusable. The systems and methods disclosed herein can reduce such impurities to acceptable levels. LPG with less than about 0.05% volume/volume high molecular weight organic impurities is desirable. In one embodiment, the LPG includes less than about 0.03% volume/volume high molecular weight organic impurities. In a more particular embodiment, the LPG includes less than 10% C16.

Activated carbon is commercially available in various forms, including granules, powders, fibers, and the like. Activated carbon powders have granules that are less than about 1 millimeter in size. Granular activated carbon (GAC) sizes can be determined using known ASTM methods and include 8×20; 20×40; 8×30 for liquid phase applications and 4×6; 4×8 or 4×10 for vapor phase applications. Activated carbon can also be combined with a binder and extruded to form extruded activated carbon (EAC). Activated carbon fibers can be characterized by their length, diameter, porosity, specific surface area, and elemental composition. Length is meant to describe the distance from end to end of a fiber. The diameter refers to the mean diameter of a fiber. Porosity is characterized by the mean pore volume within the fiber. Specific surface area is a measure of the fiber surface area, including the area within the pores, per unit of mass of fiber. Activated carbon fibers suitable for use in preparing an open channel filter include activated carbon fibers having a specific surface area between about 500 to about 1300 $m^2/g$; an average diameter between about 50 nm to about 200 micron; and an average pore size between about 5 to 500 Angstroms. Pore size and media surface area can be measured in accordance with the teachings of P. A. Ebb, C. Orr, *Analytical Methdos in Fine Particle Technology*, 1997, Micromeritics Instrument Corp. The fibers can be solid or hollow.

Preferably, the carbon media has a low capacity or no capacity (based on breakthrough testing) for low molecular weight hydrocarbons such as propane and butane and/or ordorant such as ethyl mercaptan.

In one embodiment, the carbon-containing filter element includes a pleated media in which activated carbon (for example, granular activated carbon with a mesh of 20×40 or 35×60) is combined with resin and placed between layers of scrim. Examples of suitable resins include adhesives such as polyurethane (PUR) adhesive. Suitable scrim materials include polyethersulfone (PES), polyester, or polypropylene (PP). This resulting media is flexible and can be pleated using known methods and used in connection with a cartridge system.

In another embodiment, the carbon-containing filter element is constructed as an open channel filter in which at least some of the fibers include activated carbon fiber. Methods for preparing activated carbon fiber are known and activated carbon fibers are commercially available. Suitable activated carbon fibers include fibers produced from rayon, phenolics, polyacrylonitrile. Carbon fibers can be nanofibrous and/or fall into the category of nanotubes, buckytubes, nanowires, and nanohorns. These fibrous materials can be organized in any range or combination to provide the required application performance.

In another embodiment, the carbon-containing filter element includes a formed filter in which activated carbon granules are entrapped. Suitable granular activated carbon (GAC) include granules having a size of 8×20; 20×40; or 8×30 for liquid phase applications and 4×6; 4×8 or 4×10 for vapor phase application; a surface area of at least about 500 $m^2/g$, or between about 600 $m^2/g$ to about 1200 $m^2/g$; and an average pore size of at least about 20 Angstroms, at least about 30 Angstroms, or between about 20 to 100 Angstroms.

As used herein, the term "high surface area" refers, for example, to carbon media with a surface area of at least about 500 $m^2/g$, or between about 500 $m^2/g$ to about 2300 $m^2/g$. The terms "open pore structure" and "macroporous" can be used interchangeably and refer to carbon media with an average pore size of at least about 20 Angstroms, at least about 30 Angstroms, or between about 5 to 500 Angstroms. In some implementations, from about 20 to 100 Angstroms. Examples of macroporous carbon-containing filter element include wood-, coconut-, or coal-based carbons. Pore size and media surface area can be measured in accordance with the teachings of P. A. Ebb, C. Orr, *Analytical Methdos in Fine Particle Technology*, 1997, Micromeritics Instrument Corp.

In another embodiment, the upstream filter element includes a nanofiber web in which activated carbon granules are entrapped. Suitable granular activated carbon (GAC) include granules having a size of 8×20; 20×40; or 8×30 for liquid phase applications and 4×6; 4×8 or 4×10 for vapor phase application; a surface area of at least about 500 $m^2/g$, or between about 600 $m^2/g$ to about 1200 $m^2/g$; and an average pore size of at least about 20 Angstroms, at least about 30 Angstroms, or between about 5 to 500 Angstroms. In some implementations, average pore size is from about 20 to 100 Angstroms. Suitable fibrous webs containing particulates includes those disclosed in U.S. Pat. No. 7,655,070, which issued on Feb. 2, 2010, entitled "Web Comprising Fine Fiber and Reactive, Adsorptive, or Adsorptive Particulate", incorporated by reference in its entirety.

Downstream Filter Media

The downstream media pack has a relatively low capacity for adsorbing and retaining high molecular weight contaminants, but upon reaching capacity it provides a restriction to flow of liquid through the media pack. The second filter media pack (the downstream media pack) can be formed of a material comprising a fine fiber, such as nanofiber.

In one embodiment, the downstream media pack includes a web of fibers. In a more particular embodiment, the web has relatively small pores between the fibers, e.g., less than about 25 microns, or between about 0.01 to about 25 microns, or about 0.1 to about 10 microns and, as such, provides a barrier to the passage of high molecular weight materials. The pore size measurements of the end-of-life indicator can be measured using methods described in *An Introduction to Electrospinning and Nanofibers*, pages 199 to 206 (Chapter 5), Ramakrisna et al, ISBN 981-256-4, 5-2, incorporated herein by reference in its entirety.

Once the upstream media pack becomes saturated, high molecular weight impurities begin to flow through the carbon-containing filter element downstream to the web of fibers. Because the pores of the web are too small for the high molecular weight impurities to pass, the high molecular weight impurities relatively rapidly form a film on the upstream surface of the web. The film results in an increase in backpressure, which provides an alert that the filter needs to be changed (end-of-life). The backpressure can be detected using a pressure differential sensor. Advantageously, the fiber web can also filter out carbon particles that may be shed from the filter assembly from the LPG permeate. If desired, one or more additional particulate filters can be included downstream of the filter system for the purpose of filtering out carbon particles.

In one embodiment, the fiber web includes a non-woven web of interlocking fibers. In a more particular embodiment, the fiber web includes a nanofiber or microfiber polymeric web. The term "nanofiber" as used herein refers to a fiber with a diameter less than 2000 nanometers or 2.0 micrometers. The term "microfiber" refers to a fiber with a diameter larger than 2.0 microns, but less than 10 microns. Methods for forming polymeric webs are known and include processes such as electrospinning, melt-blowing. The pore size of the web can be varied, for example, by adjusting width of the fibers, the density of the fibers and thickness of the fiber layer.

Examples of suitable nanofiber materials include polymers such as nylons, polyvinylidene chloride, polyvinylidene fluoride, polyvinylalcohol (or blends thereof) such as are described in U.S. Pat. No. 6,743,273, the disclosure of which is incorporated by reference herein. Another example of a suitable nanofiber material includes polysulfone/poly(N-vinyl lactam) alloy, such as is described in U.S. Pat. No. 7,641,055, the disclosure of which is hereby incorporated by reference herein.

Figure 6:
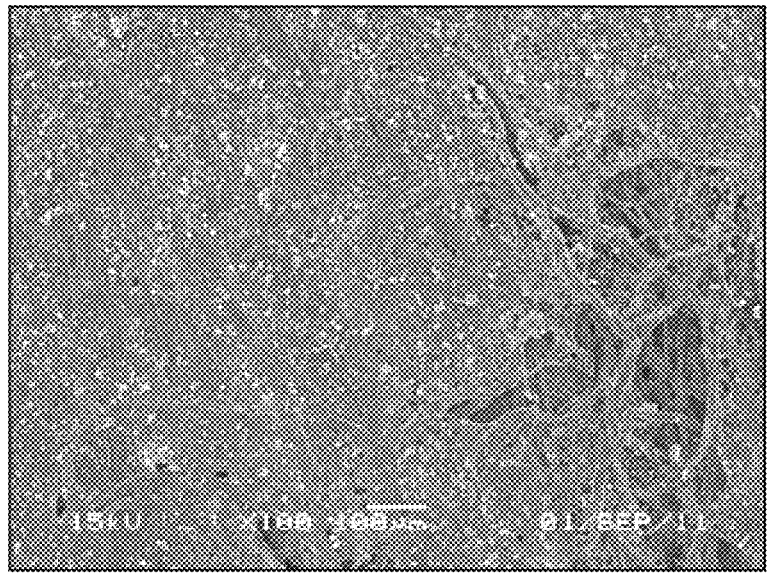
FIG. 6 is a photograph of fine fiber media showing deposits of high molecular weight hydrocarbons sufficient to substantially cover the media surface.

FIG. 6 shows a photograph of fine fiber media that has been exposed to LPG containing high molecular weight hydrocarbons. The fine fiber media has accumulated deposits of high molecular weight hydrocarbons sufficient to substantially cover the media surface. This coverage, which occurs relatively rapidly (depending upon face velocity) upon exposure to high molecular weight hydrocarbons, substantially reduces flow through the media, resulting in an increased pressure differential from the upstream to downstream side of the fine fiber media.

Particulate Filter

Figure 7:
FIG. 7 is a photograph of a particulate removal media used for removal of particulates downstream from a carbon filter element, the particulate removal media showing relatively little loading of high molecular weight hydrocarbons.

FIG. 7 is a photograph of a particulate removal media used for removal of particulates downstream from a carbon filter element, the particulate removal media showing relatively little loading of high molecular weight hydrocarbons. Suitable particulate removal media includes, without limitation, the disclosures of U.S. Pat. No. 7,314,497, entitled "Filter Medium and Structure", and U.S. Pat. No. 7,309,372, also entitled "Filter Medium and Structure", both of which are incorporated by reference in their entirety.

EXAMPLES

An activated carbon filter system was tested for its ability to filter high molecular weight organic materials from an LPG stream without adsorbing LPG itself.

The adsorption of propane was analyzed by measuring propane breakthrough and propane desorb. The results indicate that the activated carbons, particularly the macroporous ones, do not meaningfully adsorb propane, such that high molecular weight materials in the hexane (as an LPG substitute) will not have competition for absorption. Due to binding energy with the carbon media, high molecular weight organics will "kick off" propane, which is only loosely bound to the carbon surface/pore.

Figure 8:
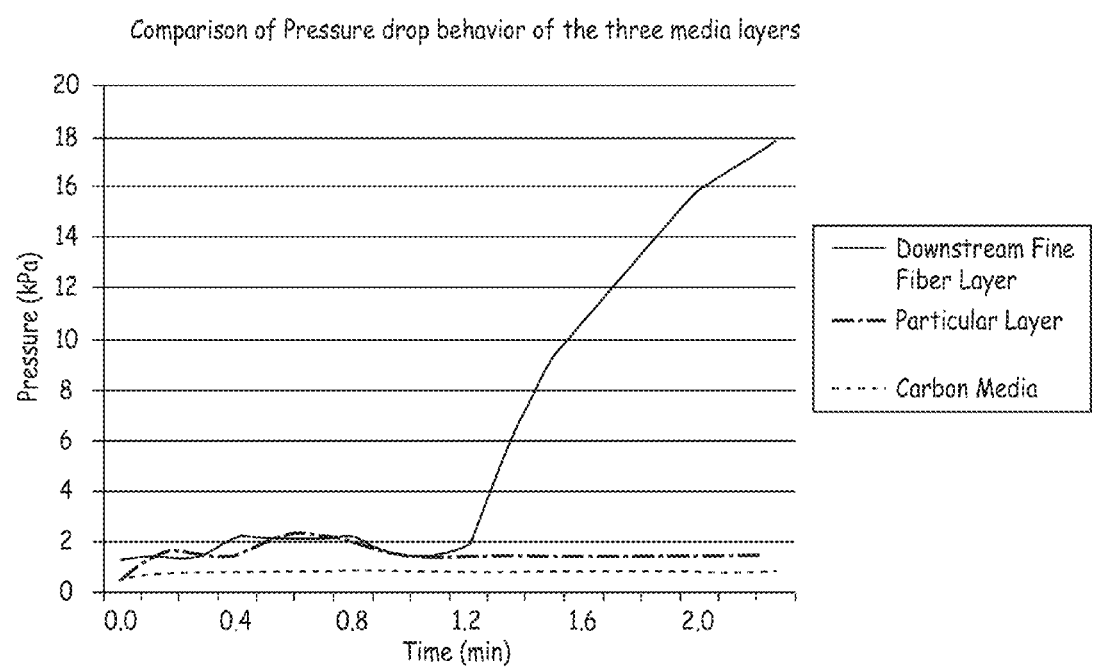
FIG. 8 is a chart showing relative pressure drop in various filter media materials that have been exposed to hexane containing high molecular weight contaminants.

To determine the change in relative pressure drops by the different filter media packs, resistance to flow was measured of various media after exposure to LPG containing high molecular weight hydrocarbons. The deposit weight of the filter was determined by subtracting the initial weight from the final weight of the filter. FIG. 8 shows relative pressure differential by the filter media of the upstream and downstream filter media packs. As is indicated, the upstream media pack of activated carbon had a much smaller change in pressure differential than the downstream fine fiber media.

Figure 9:
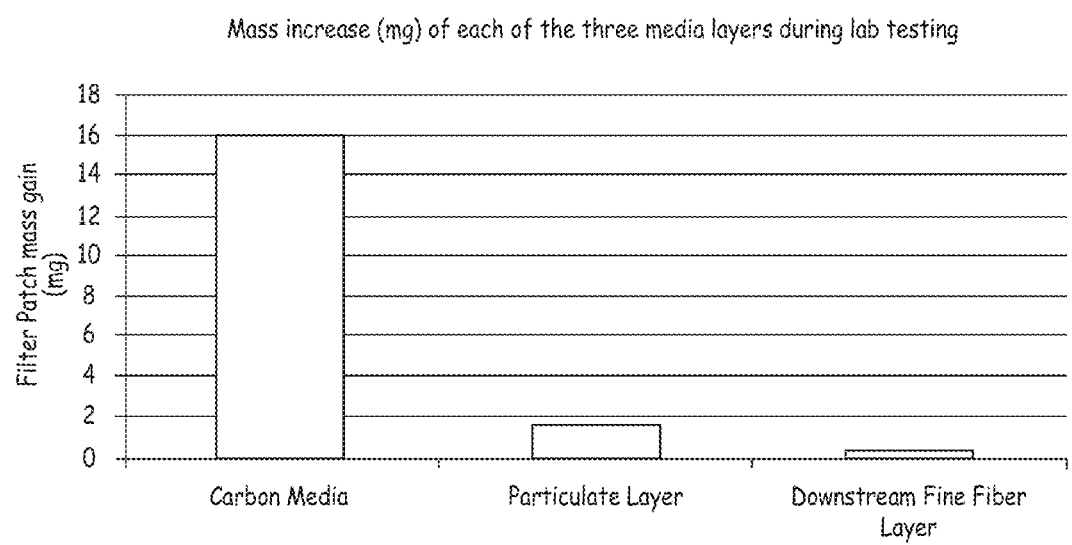
FIG. 9 is a chart showing mass gain of various filter media materials that have been exposed to hexane containing high molecular weight contaminants.

To determine the amount of high molecular weight hydrocarbons retained by the filter, the filters were weighed before and after testing. The deposit weight of the filter was determined by subtracting the initial weight from the final weight of the filter. FIG. 9 shows relative mass gain by the filter media of the upstream and downstream filter media packs exposed to hexane (as an LPGE substitute) and high molecular weight hydrocarbons. As is indicated, the upstream media pack of activated carbon had a much higher weight gain, and thus a much higher capacity.

Figure 10:
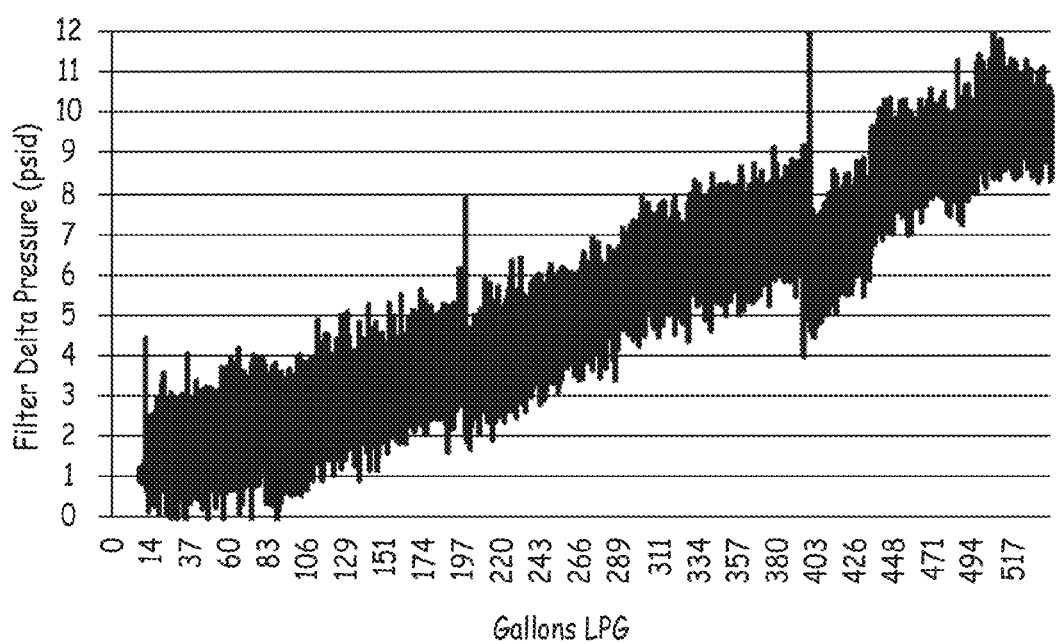
FIG. 10 is a chart showing pressure differential in a media upon exposure to liquefied petroleum gas.

FIG. 10 is a chart showing pressure differential in an element upon exposure to liquefied petroleum gas. In the embodiment shown, the carbon and particulate removal layers were wrapped layers (similar to the construction shown in FIG. 3, but with activated carbon layers and particulate removal layers wrapped), while the end of life indicator was a flat disk comprising nanofiber media positioned downstream from the activated carbon layers and particulate removal layers in the axial outlet of the filter element.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration.

The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. It should be readily apparent that any one or more of the design features described herein may be used in any combination with any particular configuration. With use of a molding process, such design features can be incorporated without substantial additional manufacturing costs. That the number of combinations are too numerous to describe, and the present invention is not limited by or to any particular illustrative combination described herein. The scope of the present subject matter should be determined with reference to the appended claims, along with the full scope of equivalents to which such claims are entitled.

What is claimed is:

1. A filter assembly for filtering high molecular weight compounds from liquefied petroleum gas, the filter assembly comprising:
   a first filter media pack configured to remove high molecular weight compounds; and
   a second filter media pack configured to remove high molecular weight compounds, the second filter media pack located downstream from the first filter media pack;
   wherein the first filter media pack is configured to exhibit a change in upstream to downstream pressure differential of less than 200 percent upon reaching its functional capacity for high molecular weight compounds,
   wherein the second filter media pack is configured to exhibit a change in upstream to downstream pressure differential of greater than 200 percent upon reaching saturation of high molecular weight compounds having more than 16 carbon atoms,
   wherein the second filter media pack comprises a web of fibers, and
   wherein the fibers have a diameter less than 2 micrometers.

2. The filter assembly of claim 1, further comprising a third media pack configured to remove solid particles from liquefied petroleum gas.

3. The filter assembly of claim 1, further comprising a third filter media pack intermediate the first filter media pack and the second filter media pack, the third filter media pack having an mean flow pore size of 10 microns or less.

4. The filter assembly of claim 1, wherein the first filter media pack comprises activated carbon.

5. The filter assembly of claim 4, wherein the first filter media pack comprises activated carbon having a surface area of at least about 500 $m^2/g$ and an average pore size of at least about 20 Angstroms.

6. The filter assembly of claim 4 wherein the first filter media pack comprises activated carbon having a surface area of between 600 $m^2/g$ and 1200 m2/g and an average pore size of at least about 20 Angstroms.

7. The filter assembly of claim 4 wherein the first filter media pack comprises activated carbon having a surface area of between 600 $m^2/g$ and 1200 m2/g and an average pore size of between 20 and 100 Angstroms.

8. The filter assembly of claim 1 wherein the high molecular weight compounds comprise hydrocarbons with between 20 and 60 carbon atoms.

9. The filter assembly of claim 1 wherein the second filter media pack has a total capacity for retaining high molecular weight hydrocarbons that is no more than 5 percent of the total capacity of the first filter media pack for retaining high molecular weight hydrocarbons.

10. The filter assembly of claim 1, wherein the second filter media pack is configured to exhibit a change in upstream to downstream pressure differential of greater than 400 percent upon reaching its functional capacity of high molecular weight compounds.

11. The filter assembly of claim 1, wherein the second filter media pack comprises a web of fibers having a pore size between the fibers of no more than about 25 microns.

12. The filter assembly of claim 1, wherein the second filter media pack comprises a web of fibers having a pore size between the fibers of no more than about 10 microns.

* * * * *